(12) United States Patent
Sieredziński et al.

(10) Patent No.: US 9,149,844 B2
(45) Date of Patent: Oct. 6, 2015

(54) METHOD AND SYSTEM FOR ARRANGING CIGARETTE PACKS

(75) Inventors: Marek Sieredziński, Radom (PL); Robert Chmielewski, Jedlnia Letnisko (PL)

(73) Assignee: INTERNATIONAL TOBACCO MACHINERY POLAND SP. Z O.O., Radom (PL)

( * ) Notice: Subject to any disclaimer, the term of this patent is extended or adjusted under 35 U.S.C. 154(b) by 41 days.

(21) Appl. No.: 13/824,006

(22) PCT Filed: Sep. 15, 2011

(86) PCT No.: PCT/PL2011/050038
§ 371 (c)(1),
(2), (4) Date: Jun. 3, 2013

(87) PCT Pub. No.: WO2012/036578
PCT Pub. Date: Mar. 22, 2012

(65) Prior Publication Data
US 2013/0240325 A1    Sep. 19, 2013

(30) Foreign Application Priority Data
Sep. 16, 2010    (PL) .......................................... 392413

(51) Int. Cl.
*B65G 47/10* (2006.01)
*B07C 5/34* (2006.01)
(Continued)

(52) U.S. Cl.
CPC . *B07C 5/34* (2013.01); *B07C 5/342* (2013.01); *B65B 19/28* (2013.01); *B65G 47/52* (2013.01); *G01N 21/8806* (2013.01)

(58) Field of Classification Search
CPC ....................................................... B07C 1/20

USPC .............. 198/370.01, 437, 382; 209/535, 536
See application file for complete search history.

(56) References Cited

U.S. PATENT DOCUMENTS 3,645,391 A * 2/1972 Hirakawa et al. .............. 209/3.3
3,939,984 A    2/1976 Butner
(Continued)

FOREIGN PATENT DOCUMENTS

CN    1377493 A    10/2002
DE    10135484 A1    1/2003
(Continued)

OTHER PUBLICATIONS

Japanese Notice of Reasons for Rejection for Japanese Application No. 2013-529095 of Jan. 6, 2015.

*Primary Examiner* — William R Harp
(74) *Attorney, Agent, or Firm* — Browdy and Neimark, PLLC

(57) ABSTRACT

Method and system for arranging cigarette packs according to the position of the filters of the cigarettes contained in the packs, each pack being provided on its outside with a detectable indicator (5), the position of the indicator on the pack (1) in relation to the filters of the cigarettes contained in the packs being predefined, in which the packs are successively delivered in the form of a first stream (7) of the packs travelling on a conveyor (6) to a detection station (8) for detecting the indicators (5) where the position of the indicator on each particular pack is detected, the packs being subsequently arranged depending on the position of the indicator (5) detected thereon by the driving means (12) controlled basing on the information concerning the position of the indicators received from the detection station (8). The arranging consists in dividing the first stream (7) of the packs into at least two separate streams of the travelling packs.

8 Claims, 6 Drawing Sheets

(51) Int. Cl.
*B07C 5/342* (2006.01)
*B65B 19/28* (2006.01)
*G01N 21/88* (2006.01)
*B65G 47/52* (2006.01)

(56) References Cited

U.S. PATENT DOCUMENTS

| | | | |
|---|---|---|---|
| 4,530,199 A | | 7/1985 | Manservisi et al. |
| 4,622,875 A | * | 11/1986 | Emery et al. .................. 83/80 |
| 5,240,117 A | | 8/1993 | Focke et al. |
| 5,275,295 A | * | 1/1994 | Eisenlohr et al. ............ 209/536 |
| 5,887,699 A | * | 3/1999 | Tharpe ........................ 198/367 |

FOREIGN PATENT DOCUMENTS

| | | |
|---|---|---|
| EP | 0481191 A1 | 4/1992 |
| EP | 0509270 A2 | 10/1992 |
| EP | 0562349 A | 9/1993 |
| FR | 2565074 A1 | 12/1985 |
| GB | 2447353 A | 9/2008 |
| JP | 53040968 A | 4/1978 |
| JP | 61124420 A2 | 6/1986 |
| JP | 05120315 A | 5/1993 |
| JP | 07291205 A | 11/1995 |
| JP | 11001214 A2 | 1/1999 |
| WO | 0179092 A1 | 10/2001 |
| WO | 0204297 A | 1/2002 |

* cited by examiner

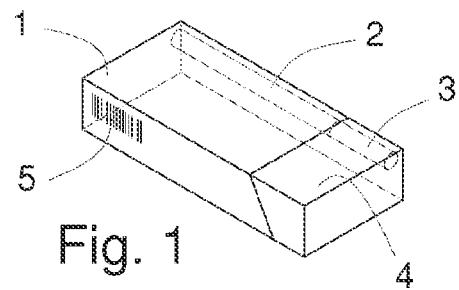
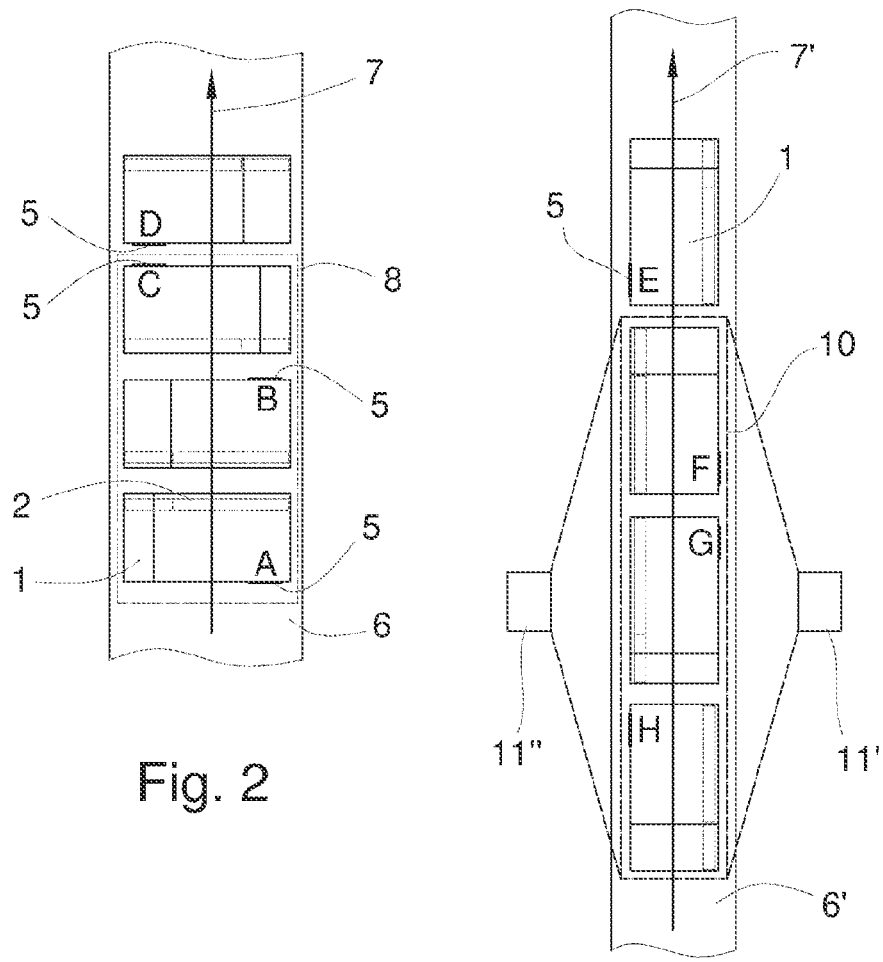

METHOD AND SYSTEM FOR ARRANGING CIGARETTE PACKS

The present invention relates to a method and a system for arranging packs containing cigarettes.

Cigarette packs are typically transported on conventional conveyors in an orderly way i.e. they are oriented on the conveyor all in the same direction and travel as a stream of packs. During production a situation may occur where the packs that were previously removed from the production line need to be placed there again in an orderly way, which means that they should be delivered back to the conveyor as a stream of packs or one by one.

An arranged stream of packs is also required in the case of delivering packs constituting production waste to a location for recovering tobacco from the cigarettes contained in the packs. In EP 0 481 191 an apparatus is disclosed for removing cigarettes from a pack constituting production waste in which cigarette filters are cut off from the tobacco part of the cigarettes by way of cutting the pack with a disc knife. However, this document discloses neither a method nor an apparatus enabling orderly delivery of the packs in which all the filters would always be located by the same side. Similar apparatuses disclosed in FR 2 565 074 and DE 101 35 484 require the packs to be delivered in an orderly way. In all these apparatuses the packs that are cut must be delivered in an orderly way.

The object of the invention is to provide a method and a system for arranging cigarette packs that are travelling on a conveyor as a stream of non-uniformly oriented packs, in which after the packs have been arranged, the cigarette filters of the cigarettes contained therein are all uniformly oriented.

According to the invention a method is provided for arranging cigarette packs according to the position of the filters of the cigarettes contained in the packs, each pack being provided on its outside with a detectable indicator, the position of the indicator on the pack in relation to the filters of the cigarettes contained in the packs being predefined, in which the packs are successively delivered as a first stream of the packs travelling on a conveyor to a detection station for detecting the indicators where the position of the indicator on each particular pack is detected, the packs being subsequently arranged depending on the position of the indicator detected thereon by the driving means controlled basing on the information concerning the position of the indicators received from the detection station, the arranging of the cigarette packs consisting in dividing the first stream of the packs into at least two separate streams of the travelling packs.

The packs are preferably arranged by directing them to the respective streams through shifting at least some of the selected packs out of the first stream on the conveyor.

The driving means preferably include at least one actuator.

The positions of the indicators are preferably detected by a detection station including at least one scanner.

The indicators may be selected form a group including: a bar code, a code made with a UV paint, a code comprising ferromagnetic elements, a hologram and combination thereof.

In an advantageous embodiment the packs are transported to the detection station, their position on the conveyor being transversal to the direction of movement of the conveyor, and the packs are arranged by dividing them into at most two streams of packs, one of the streams containing only the packs having the indicators located by the same side of the conveyor with relation to its longitudinal axis, and the other stream containing only the packs having the indicators located by the opposite side of the conveyor with relation to its longitudinal axis.

In another embodiment the packs are transported to the detection station, their position on the conveyor being transversal to the direction of movement of the conveyor, and the packs are arranged by dividing them into 1, 2, 3 or 4 streams of packs, each of the streams containing the packs having their indicators on different locations on the pack, the first stream containing only the packs with a first location of the indicator, the second stream containing only the packs with a second location of the indicator, the third stream containing only the packs with a third location of the indicator, and the fourth stream containing only the packs with a fourth location of the indicator.

Optionally, the packs are transported to the detection station in a position on the conveyor along the direction of movement of the conveyor, and the packs are arranged by dividing them into at most two streams of packs, one of streams containing only the packs having the indicators located in the front part of the pack with relation to its direction of movement, and the other stream containing only the packs having the indicators located on the rear part of the pack with relation to its direction of movement.

In yet another embodiment of the method according to the invention the packs are transported to the detection station, their position on the conveyor being along the direction of movement of the conveyor, and the packs are arranged by dividing them into 1, 2, 3 or 4 streams of packs, each of the streams containing the packs having the indicators on different locations on the pack, the first stream containing only the packs with a first location of the indicator, the second stream containing only the packs with a second location of the indicator, the third stream containing only the packs with a third location of the indicator, and the fourth stream containing only the packs with a fourth location of the indicator.

The invention also provides a system for arranging cigarette packs according to the positions of the filters of the cigarettes contained in the packs, each pack being provided on its outside with a detectable indicator, the position of the indicator on the pack in relation to the filters of the cigarettes contained in the packs being predefined, comprising at least one conveyor on which the packs are successively transported, a detection station for detecting the indicators enabling determination of the position of each transported pack, and driving means controlled basing on the information concerning the position of the indicators received from the detection station.

Preferably, the driving means include at least one actuator.

The positions of the indicators are preferably detected by the detection station comprising at least one scanner.

The present invention is based on an unexpected advantage realized by the inventors, resulting from the fact that cigarette packs are provided with indicators, e.g. bar codes, that are always positioned on the opposite side of the pack with relation to the filters of the cigarettes contained within. Special indicators may also be placed on the packs during production in order to enable positioning of the packs. This feature, when used according to the present invention, enables the arrangement of the packs according to the positions of the filters. In case of the packs that were previously removed from a production line and need to be placed there again in an orderly way, it is surprisingly convenient to detect their positions using a scanner and the indicators that are present on the packs by default.

The system and the method according to the invention are illustrated in a preferred embodiment presented in the appended drawing, in which:

FIG. 1 shows a cigarette pack in a perspective view;

FIG. 2 shows the cigarette packs travelling on a conveyor of the system, their orientation being transversal to the direction of movement;

FIG. 3 shows the cigarette packs travelling on a conveyor of the system, their orientation being along the direction of movement;

Figure 4:
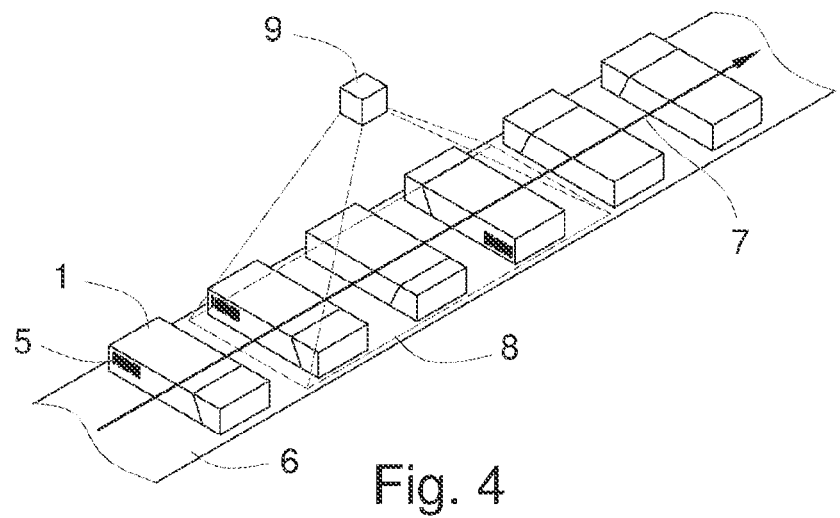
FIG. 4 shows a perspective view of the system with one detector and a conveyor carrying the packs that are oriented transversally to the direction of movement.

For the sake of simplicity three expressions defining the walls of the packs will be used hereafter: bottom—the wall perpendicular to the cigarette axes having the smallest surface area, side wall—the smaller wall parallel to the cigarette axes, front wall—the bigger wall parallel to the cigarette axes.

FIG. 1 presents an exemplary cigarette pack 1, the position of the cigarette filters in the pack having been shown by means of a cigarette 2 indicated by dotted lines. The filter 3 is located on the side of the end wall constituting an openable lid 4. An indicator 5 in the form of a bar code is located on a side wall near the bottom that is opposite to the filter 3. The indicator 5 may have a form of any sign made by means of e.g. paint UV, it may comprise ferromagnetic elements, or it may be a hologram or a graphic sign dectectable by optoelectronic means.

Figure 5:
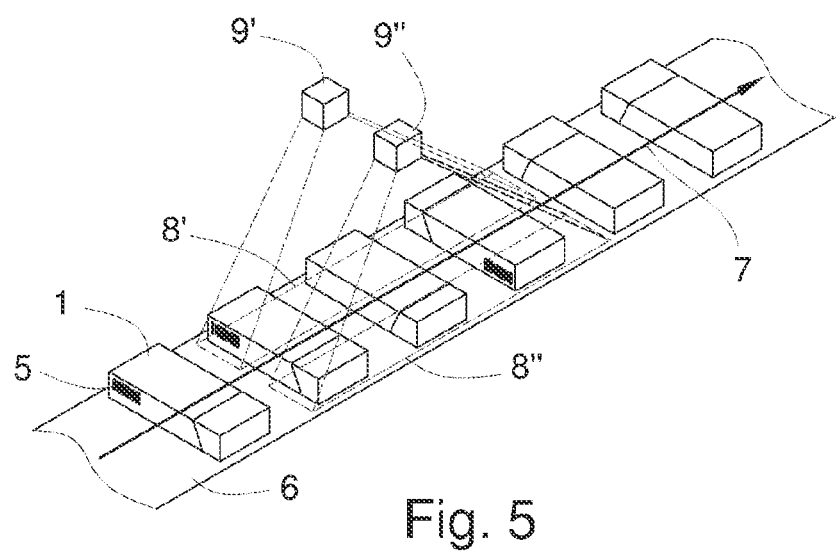
FIG. 5 shows a perspective view of the system with two detectors and a conveyor carrying the packs that, are oriented transversally to the direction of movement.

FIG. 2 presents the packs 1 located on a conveyor 6. The packs travelling as a first stream, their side walls being transversal to the direction of movement 7 of the conveyor 6, the packs 1 having been previously uniformly oriented by a device (not shown) which aligned them lying on the conveyor with their front walls facing the conveyor, their side walls being parallel to each other. During their travel on the conveyor 6, the packs 1 pass through a station 8 for detecting of the indicators 5, e.g. bar codes. As shown in FIGS. 4 and 5, the area of the station 8 for detecting of the indicators 5 is delimited by the operational area of a scanner 9 located above the conveyor 6. A conventional control system, for example a system comprising a controller PLC (not shown) receives the data about the position of the indicators 5 on the packs 1 from the detection station 8. Each pack 1, after having passed the detection station 8 will have information attributed concerning the actual position of the indicator on its left or right side wall with respect to the direction of movement 7 of the conveyor 6 and another information saying whether the indicator 5 is located in the front or the rear part of the pack 1. The use of "front" and "rear" herein relates to packs moving in the direction 7. All possible positions of the packs on the conveyor have been designated by A, B, C and D (A—the indicator on the rear right side, B—the indicator on the front right side, C—the indicator on the front left side, D—the indicator on the rear left side).

FIG. 3 presents a conveyor 6' with the packs 1 transported thereon forming a first stream, their side walls moving along the direction of movement 7' of the conveyor 6', the packs 1 having been previously uniformly oriented by a device (not shown) which aligned them lying on the conveyor with their front walls facing the conveyor, their side walls being parallel to each other. During their travel on the conveyor 6', the packs 1 pass through a station 10 for detecting of the indicators 5. The area of the station 10 for detecting of the indicators 5 is delimited by the operational area of scanners 11' and 11" located laterally to the conveyor 6'. A control system receives the data about the position of the indicators on the packs 1 from the detection station 10. Each pack 1 after having passed the detection station 10 will have information attributed concerning the actual position of the indicator on its left or right side wall with respect to the direction of movement 7' of the conveyor 6' and another information saying whether the indicator 5 is located in the front or the rear part of the pack 1. The use of "front" and "rear" herein relates to packs moving in the direction 7'. All possible positions of the packs on the conveyor have been designated by E, F, G and H (E—the indicator on the rear left side, F—the indicator on the rear right side, G—the indicator on the front right side, H—the indicator on the front left side).

FIG. 4 presents the conveyor 6 with the packs 1 transported thereon, the detection station 8 being equipped with one scanner 9. The scanner is shown as a compact block for the sake of simplicity; in a real industrial embodiment it may have a different form.

FIG. 5 presents the conveyor 6 with the packs 1 transported thereon, the detection station 8 consisting of the parts 8' and 8" is equipped with two scanners 9' and 9". An embodiment of the invention making use of just one scanner 9' or 9" is also possible, in which case the detection station 8' or 8" is located over a half-part of the conveyor only. In such case only the indicators 5 located on one side of the packs (and the conveyor) are detected, in the rear or the front part thereof. Hence, if no indicator 5 is detected on a pack 1, an indicator 5 must be located on the opposite side of the pack (conveyor) which also defines the position of the cigarette filters 3 within the pack 1.

Figure 6:
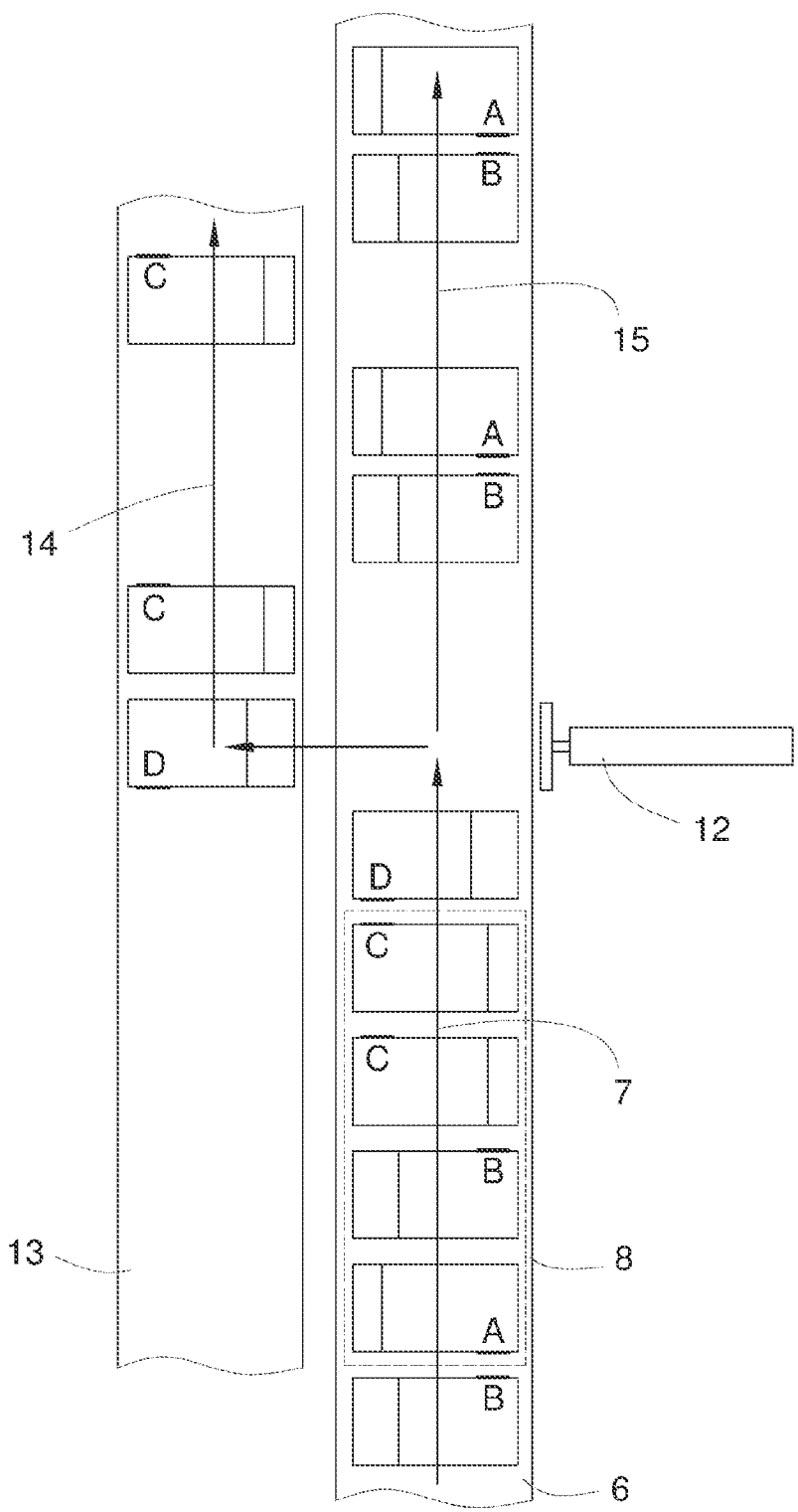
FIG. 6 shows how the packs are arranged, while travelling with their orientation transversal to the direction of movement, the first stream of packs being divided, into two streams.

FIG. 6 shows a conveyor 6 with the packs 1 transported thereon forming a first stream along the direction of movement. 7, the packs being oriented transversally to the direction of movement 7. The packs 1 pass through the station 8 for detection of the position of the indicators 5 on the packs 1. The data concerning the position of the indicators 5 on the packs is transmitted to a typical (not shown) control unit and then to the driving means. The driving means consisting of an actuator 12 are designed to direct the packs 1 having the indicators 5 located on the left side of the conveyor 6, with relation to its longitudinal axis, i.e. the packs designated by C and D, onto the conveyor 13 where the second stream of the packs is formed travelling in the direction 14. The packs designated by A and B travel on as a continuation of the first stream moving in the direction 15. The presence and the number of the packs in both streams depend on the random choice of the positions of the packs travelling on the conveyor in the first stream 7.

Figure 7:
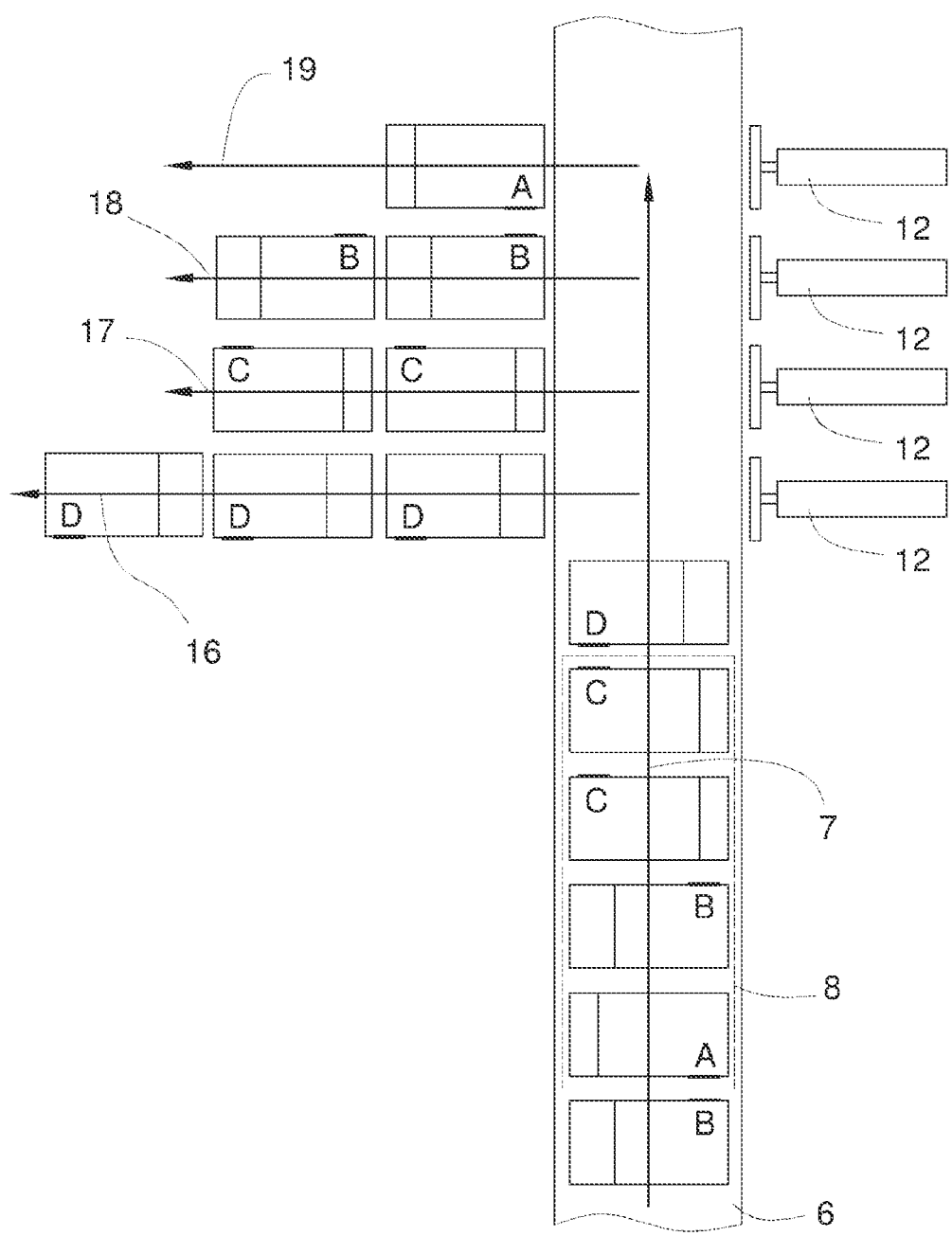
FIG. 7 shows now the packs are arranged while travelling with their orientation transversal to the direction of movement, the first stream of packs being divided into four streams.

In FIG. 7 the packs also travel as the first stream on the conveyor 6 positioned transversally to the direction 7 and pass through the detection station 8. Depending on the information concerning the position of the indicators 5 on the packs 1, suitable driving means consisting of the four actuators 12 direct the packs to the streams foreseen for the specific positions of the packs 1 designated by A, B, C and D. The packs 1 in the particular streams travel along the respective directions 16, 17, 18 and 19. The presence and the number of the packs in the streams depend on the random choice of the positions of the packs travelling on the conveyor in the first stream 7.

Figure 8:
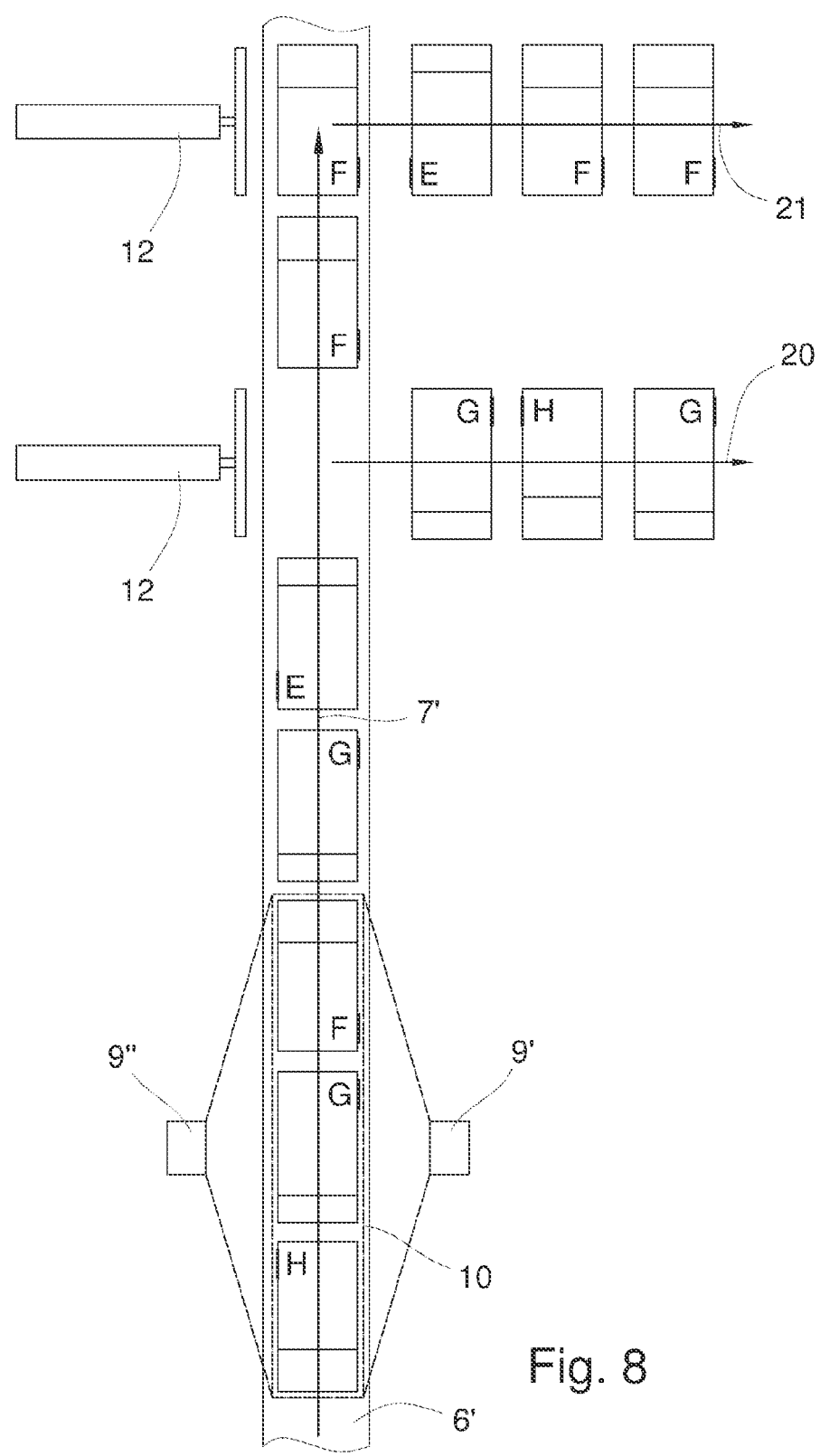
FIG. 8 shows how the packs are arranged while travelling with their orientation along the direction of movement, the first stream of packs being divided into two streams.
Figure 9:
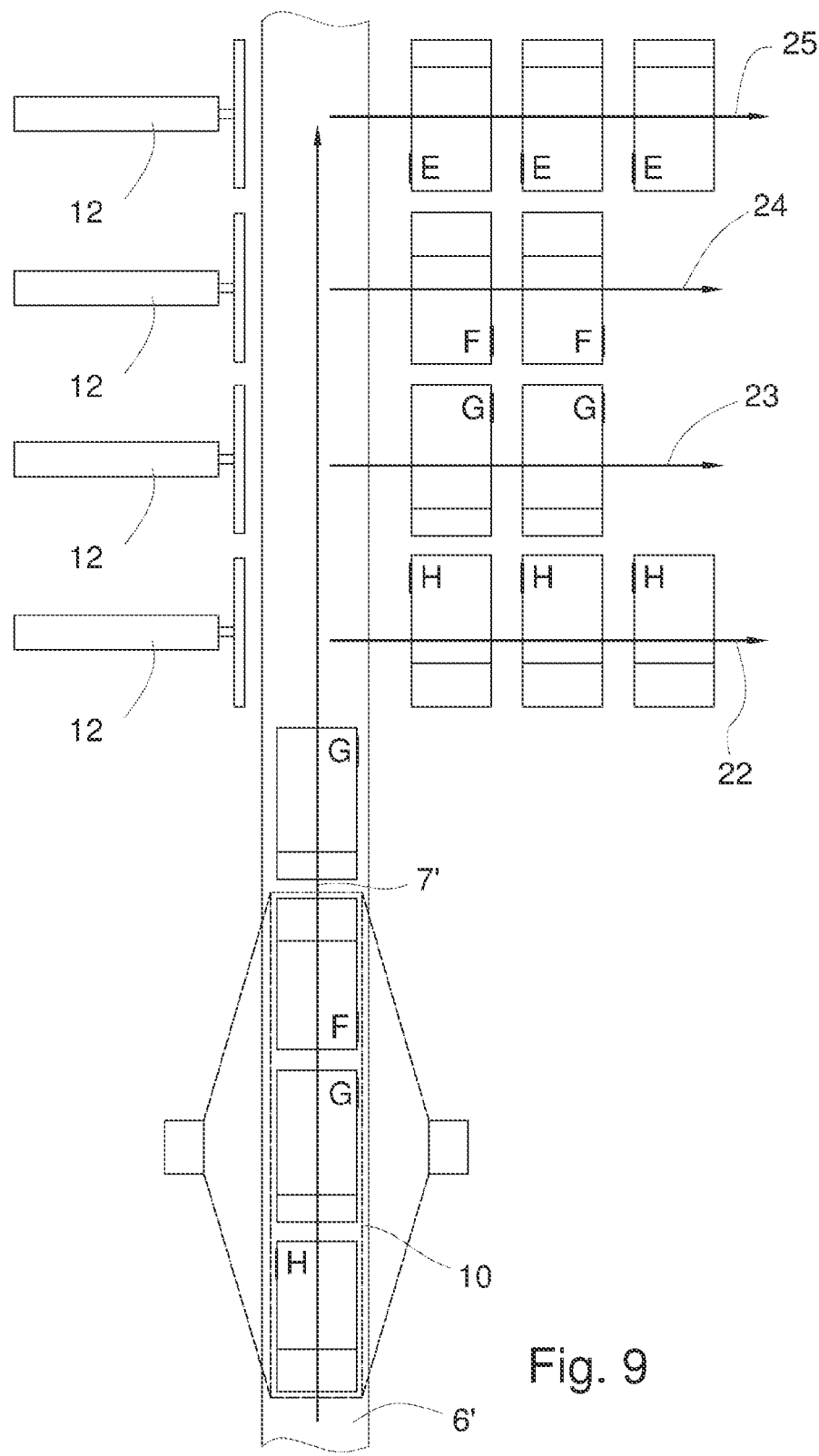
FIG. 9 shows how the packs are arranged while travelling with their orientation along the direction of movement, the first stream of packs being divided into four streams.

FIG. 8 shows a conveyor 6' with the packs 1 transported thereon forming a first stream along the direction of movement 7', the packs 1 being oriented along the direction of movement 7'. The packs pass through the station 10 for detection of the position of the indicators 5 on the packs 1. The data concerning the position of the indicators 5 on the packs is transmitted to a typical (not shown) control unit and then to the driving means. The driving means consisting of one of the actuators 12 are designed to direct the packs 1 having the indicators 5 located in the front part, with relation to the direction of movement 7', i.e. the packs designated by G and H, into a second stream of the packs travelling in the direction 20. The packs designated by E and F travel on to be directed by the other of the actuators 12 to a stream moving in the direction 21. In FIG. 9 the packs 1 also travel in the first stream on the conveyor 6' positioned along the direction of movement 7' and pass through the detection station 10. Depending on the information concerning the position of the indicators 5 on the packs 1, suitable driving means consisting of the four actuators 12 direct the successive packs to the streams foreseen for the specific positions of the packs 1 designated by E, F, G and H. The packs 1 in the particular streams travel along the respective directions 22, 23, 24 and 25.

The driving means may consist of the above described actuators shifting the packs out of the first stream, but they may also have the form of any suitable technical means enabling division of the first stream of the packs into at least two separate streams.

The detection station may comprise at least one detector, e.g. a scanner or other means suitable for detection of the indicators depending on their type.

The invention claimed is:

1. A method of arranging cigarette packs, each pack being provided on its outside with a detectable indicator, comprising:
   successively delivering the packs as a first stream of the packs travelling on a conveyor to a detection station for detecting the indicators where the position of the indicator on each particular pack is detected,
   subsequently arranging the packs depending on the position of the indicator detected thereon by at least one actuator controlled based on the information concerning the position of the indicators received from the detection station,
   wherein the position of the indicator on the pack in relation to the filters of the cigarettes contained in the packs is predefined such that the position of the indicator on the pack indicates the position of the filters of the cigarettes in the pack, and the first stream of the cigarette packs is divided into at least two separate streams of the travelling packs, so that each stream comprises the packs selected according to a different position of the filters of cigarettes contained in the packs.

2. The method of claim 1, wherein the packs are arranged by directing them to the respective streams through shifting at least some of the selected packs out of the first stream on the conveyor.

3. The method of claim 1, wherein the positions of the indicators are detected by a detection station including at least one scanner.

4. The method of claim 1, wherein the indicators are selected form a group including: a bar code, a code made with a UV paint, a code comprising ferromagnetic elements, a hologram and combination thereof.

5. The method according to claim 1, further comprising transporting the packs to the detection station, the packs being positioned on the conveyor such that longer sides of the packs are transverse to the direction of movement (7) of conveyor (6), and
   arranging the packs by dividing them into at most two streams of packs, one of the streams containing only the packs (A, B) having the indicators located by the same side of the conveyor with relation to its longitudinal axis, and the other stream containing only the packs (C, D) having the indicators located by the opposite side of the conveyor with relation to its longitudinal axis.

6. The method according to claim 1, further comprising transporting the packs to the detection station, the packs being positioned on the conveyor such that longer sides of the packs are transverse to the direction of movement (7) of conveyor (6), and
   arranging the packs by dividing them into 1, 2, 3 or 4 streams of packs, each of the streams containing the packs having the indicators on different locations on the pack, the first stream containing only the packs (A), the second stream containing only the packs (B), the third stream containing only the packs (C), the fourth stream containing only the packs (D).

7. The method according to claim 1, further comprising transporting the packs to the detection station in a position on the conveyor such that longer sides of the packs are disposed along the direction of movement (7) of the conveyor (6), and
   arranging the packs by dividing them into at most two streams of packs, one of the streams containing only the packs (G, H) having the indicators located in the front part of the pack with relation to its direction of movement, and the other stream containing only the packs (E, F) having the indicators located on the rear part of the pack with relation to its direction of movement.

8. The method according to claim 1, further comprising transporting the packs to the detection station in a position on the conveyor such that longer sides of the packs are disposed along the direction of movement (7) of the conveyor (6), and
   arranging the packs by dividing them into 1, 2, 3 or 4 streams of packs, each of the streams containing the packs having the indicators on different locations on the pack, the first stream containing only the packs (E), the second stream containing only the packs (F), the third stream containing only the packs (G), the fourth stream containing only the packs (H).

* * * * *